(12) United States Patent
Umezawa et al.

(10) Patent No.: US 10,695,006 B2
(45) Date of Patent: Jun. 30, 2020

(54) APPARATUS AND DISPLAY CONTROL METHOD

(71) Applicant: CANON KABUSHIKI KAISHA, Tokyo (JP)

(72) Inventors: Kohtaro Umezawa, Tokyo (JP); Takuji Oishi, Kawasaki (JP); Yoshiko Nakamura, Kusatsu (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 114 days.

(21) Appl. No.: 15/577,996

(22) PCT Filed: Jun. 16, 2016

(86) PCT No.: PCT/JP2016/068585
§ 371 (c)(1),
(2) Date: Nov. 29, 2017

(87) PCT Pub. No.: WO2016/208647
PCT Pub. Date: Dec. 29, 2016

(65) Prior Publication Data
US 2018/0289335 A1 Oct. 11, 2018

(30) Foreign Application Priority Data
Jun. 23, 2015 (JP) ................................ 2015-125787

(51) Int. Cl.
*A61B 5/1455* (2006.01)
*A61B 5/00* (2006.01)
(Continued)

(52) U.S. Cl.
CPC ............ *A61B 5/743* (2013.01); *A61B 5/0037* (2013.01); *A61B 5/0095* (2013.01);
(Continued)

(58) Field of Classification Search
None
See application file for complete search history.

(56) References Cited

U.S. PATENT DOCUMENTS

| 8,657,737 B2 | 2/2014 | Saito |
| 9,330,462 B2 | 5/2016 | Oishi |

(Continued)

FOREIGN PATENT DOCUMENTS

| CN | 102188226 | 9/2011 |
| CN | 102197982 | 9/2011 |

(Continued)

OTHER PUBLICATIONS

Wang et al., "Photoacoustic Tomography: In Vivo Imaging from Organelles to Organs" Science, Mar. 23, 2012, vol. 335, pp. 1-11. (Discussed at specification paragraph [0005]).

*Primary Examiner* — Eric F Winakur
*Assistant Examiner* — Marjan Fardanesh
(74) *Attorney, Agent, or Firm* — Venable LLP

(57) ABSTRACT

The present invention employs an apparatus that includes a first acquisition unit that acquires information relating to an oxygen saturation distribution, a determination unit that determines, based on the information relating to the oxygen saturation distribution, whether a calculated value of an oxygen saturation at each of a plurality of positions is included in a first numerical range from 100% to a first value more than 100% or a second numerical range more than the first value, and a display control unit that causes a display unit to display an image of the oxygen saturation distribution so as to be able to distinguish whether the calculated value of the oxygen saturation at each position is included in the first or second numerical range based on a determination result.

19 Claims, 6 Drawing Sheets

(51) Int. Cl.
*A61B 5/145* (2006.01)
*G06T 11/00* (2006.01)
*A61B 8/00* (2006.01)
*A61B 8/08* (2006.01)

(52) U.S. Cl.
CPC .......... *A61B 5/14542* (2013.01); *A61B 5/489* (2013.01); *A61B 5/7203* (2013.01); *A61B 5/7278* (2013.01); *A61B 5/0035* (2013.01); *A61B 5/0075* (2013.01); *A61B 8/085* (2013.01); *A61B 8/4483* (2013.01); *A61B 2576/00* (2013.01); *G06T 11/001* (2013.01); *G06T 2210/41* (2013.01)

(56) References Cited

U.S. PATENT DOCUMENTS

| | | |
|---|---|---|
| 9,360,551 B2 | 6/2016 | Umezawa et al. |
| 9,519,980 B2 | 12/2016 | Oishi |
| 9,579,085 B2 | 2/2017 | Fukutani et al. |
| 9,741,111 B2 | 8/2017 | Oishi |
| 2011/0237884 A1 | 9/2011 | Saito |
| 2011/0245652 A1 | 10/2011 | Oishi |
| 2012/0289812 A1 | 11/2012 | Oishi |
| 2013/0035570 A1 | 2/2013 | Miyasato |
| 2013/0160558 A1 | 6/2013 | Oishi |
| 2014/0018645 A1 | 1/2014 | Wada et al. |
| 2014/0058245 A1 | 2/2014 | Oishi et al. |
| 2014/0182384 A1 | 7/2014 | Watanabe et al. |
| 2014/0187924 A1 | 7/2014 | Oishi |
| 2014/0316236 A1 | 10/2014 | Umezawa |
| 2015/0256761 A1 | 9/2015 | Umezawa |
| 2016/0022149 A1 | 1/2016 | Asao et al. |
| 2016/0184133 A1 | 6/2016 | Miyasato et al. |
| 2016/0189375 A1 | 6/2016 | Nanaumi et al. |
| 2017/0055842 A1 | 3/2017 | Umezawa |
| 2017/0055843 A1 | 3/2017 | Umezawa |
| 2017/0055844 A1 | 3/2017 | Umezawa et al. |
| 2017/0086678 A1 | 3/2017 | Oishi |
| 2017/0095155 A1 | 4/2017 | Nakajima et al. |
| 2017/0143278 A1 | 5/2017 | Nakamura |
| 2017/0172419 A1 | 6/2017 | Oishi et al. |
| 2017/0311810 A1 | 11/2017 | Nakamura |
| 2017/0332913 A1 | 11/2017 | Nakamura |

FOREIGN PATENT DOCUMENTS

| | | |
|---|---|---|
| CN | 102908164 | 2/2013 |
| CN | 103908226 | 7/2014 |
| EP | 2465431 | 6/2012 |
| EP | 2749209 | 7/2014 |
| JP | 2014-128321 | 7/2014 |

ABSORPTION COEFFICIENT DISTRIBUTION IMAGE (λ1nm)
301

ABSORPTION COEFFICIENT DISTRIBUTION IMAGE (λ2nm)
302

OXYGEN SATURATION DISTRIBUTION IMAGE (DISPLAY WITH 0% TO 150%)
303

IMAGE DISPLAYING AREA OF OXYGEN SATURATION OF 0% TO 100% (COMPARATIVE EXAMPLE)
304

IMAGE DISPLAYING AREA OF OXYGEN SATURATION OF 0% TO 120%
305

APPARATUS AND DISPLAY CONTROL METHOD

TECHNICAL FIELD

The present invention relates to an apparatus and a display control method.

BACKGROUND ART

In the field of medicine, a study of imaging of function information as physiological information on a biological body is recently conducted. Photoacoustic imaging (PAI) is one of imaging techniques of the function information.

In the photoacoustic imaging, pulsed light generated from a light irradiation unit (light source) is applied to an object. When energy of the applied light that has propagated and diffused in the object is absorbed by a light absorber in the object (e.g., a blood vessel or a skin), an acoustic wave is generated by a photoacoustic effect (hereinafter referred to as a photoacoustic wave). A reception signal converted from the photoacoustic wave by a conversion element is subjected to analysis processing by an information processing apparatus, and an optical characteristic distribution inside the object is thereby acquired. By converting the optical characteristic distribution into image data and displaying the image data, information useful for diagnosis or the like is obtained.

The optical characteristic distribution includes the distribution of a sound pressure generated by light absorption (initial sound pressure distribution) and an absorption coefficient distribution of the light. By applying a plurality of pulsed light beams having different wavelengths to determine the absorption coefficient of the light beam of each wavelength, a concentration relating distribution of a substance that exists in the object (the distribution of values relating to the concentration of the substance) is obtained.

The concentration relating distribution includes the distribution of the content of oxyhemoglobin to total hemoglobin in blood, i.e., an oxygen saturation distribution in blood as disclosed in NPL 1. This is a value determined based on the result of acquisition of respective contents by using a difference in light absorption spectrum between deoxyhemoglobin and oxyhemoglobin to compare spectrums measured with different wavelengths. By determining the oxygen saturation at each position in the object, the oxygen saturation distribution is acquired. In addition, in NPL 1, the oxygen saturation of not less than 0% and not more than 100% is displayed with a hue corresponding to the value of the oxygen saturation.

CITATION LIST

Non Patent Literature

NPL 1: L. V. Wang, et al. "Photoacoustic Tomography: In Vivo Imaging from Organelles to Organs" Science, Vol 335 (March 2012)

SUMMARY OF INVENTION

Technical Problem

Incidentally, there are cases where a value other than an expected value is calculated in a characteristic information distribution due to a calculation error of the characteristic information distribution obtained by a photoacoustic apparatus. In these cases, there is a possibility that diagnostic performance by the photoacoustic apparatus is reduced.

The present invention has been made in view of the above problem. An object of the present invention is to provide a technique for preventing a reduction in diagnostic performance even in the case where an unexpected value is included in the characteristic information distribution of the object acquired by the photoacoustic apparatus.

Solution to Problem

The present invention provides an apparatus comprising:
a first acquisition unit configured to acquire information relating to an oxygen saturation distribution;
a determination unit configured to determine, based on the information relating to the oxygen saturation distribution, whether a calculated value of an oxygen saturation at each of a plurality of positions is included in a first numerical range from 100% to a first value more than 100% or a second numerical range in which an included value is more than the first value; and
a display control unit configured to cause a display unit to display an image of the oxygen saturation distribution so as to be able to distinguish whether the calculated value of the oxygen saturation at each of the plurality of positions is included in the first numerical range or the second numerical range based on a determination result of the determination unit.

The present invention also provides a display control method for an image of an oxygen saturation distribution, comprising the step of causing a display unit to display the image of the oxygen saturation distribution so as to be able to distinguish between a position corresponding to a numerical range in which a calculated value of an oxygen saturation is from 100% to a first value more than 100% and a position corresponding to a second numerical range in which the calculated value of the oxygen saturation is more than the first value.

Advantageous Effects of Invention

According to the present invention, it is possible to provide the technique for preventing the reduction in diagnostic performance even in the case where the unexpected value is included in the characteristic information distribution of the object acquired by the photoacoustic apparatus.

Further features of the present invention will become apparent from the following description of exemplary embodiments with reference to the attached drawings.

DESCRIPTION OF EMBODIMENTS

Figures 1A, 1B:
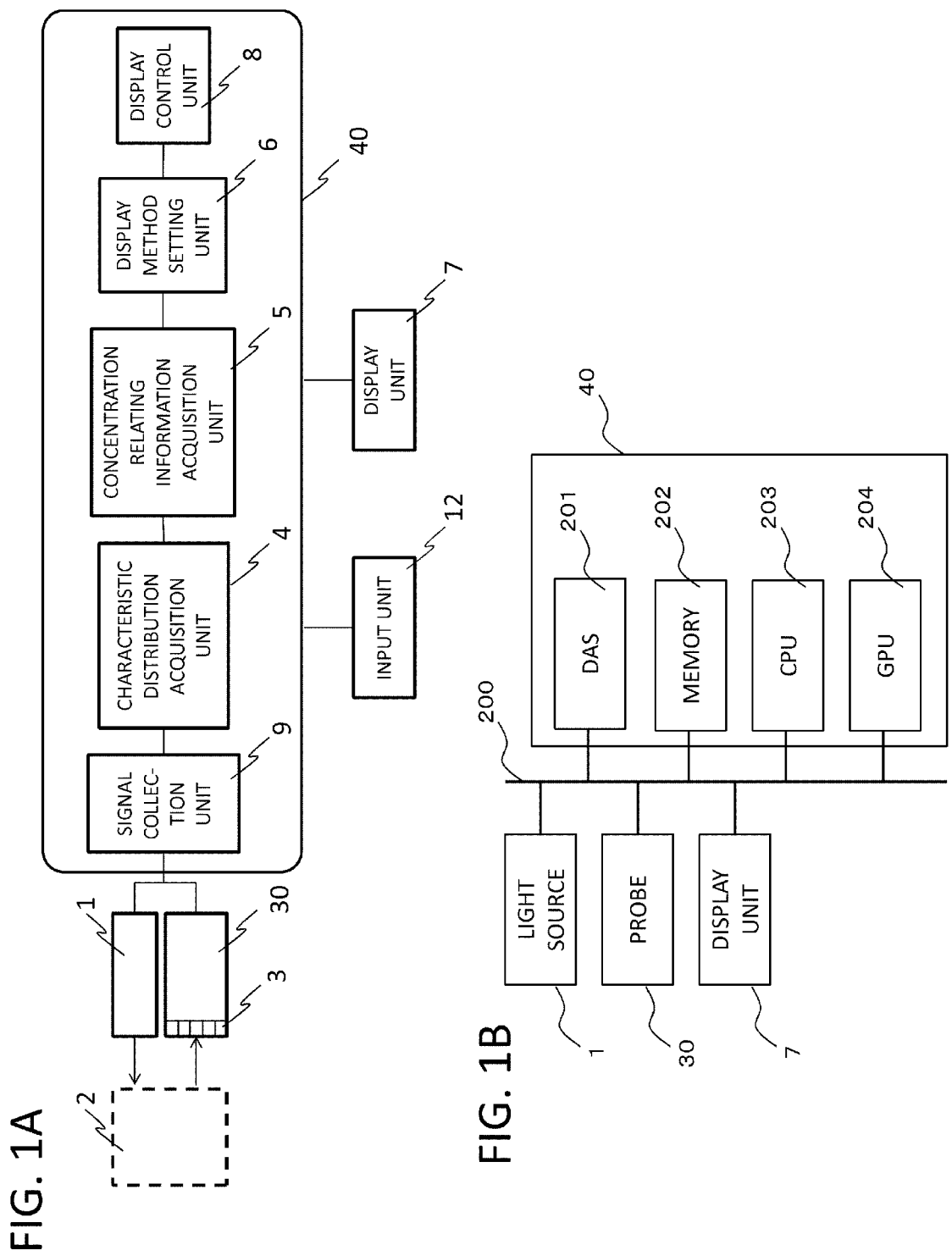
FIG. 1A and FIG. 1B are schematic views showing a configuration of a photoacoustic apparatus.

Hereinbelow, preferred embodiments of the present invention will be described with reference to the drawings.

However, the dimension, material, shape, relative arrangement and the like of each component described below should be appropriately changed according to the configuration and various conditions of an apparatus to which the invention is applied. Therefore, the scope of the invention is not limited to the following description.

The present invention relates to a technique for detecting an acoustic wave propagating from an object, and generating and acquiring characteristic information on the inside of the object. Therefore, the present invention is viewed as an object information acquisition apparatus or its control method, or an object information acquisition method or a signal processing method, or a display control method. The present invention is also viewed as a program for causing an information processing apparatus provided with hardware resources such as a CPU and a memory to execute these methods or a storage medium that stores the program. The storage medium may be a non-transitory computer readable storage medium that stores the program.

The object information acquisition apparatus of the present invention includes an apparatus (photoacoustic apparatus) utilizing a photoacoustic effect that receives an acoustic wave generated in an object by applying light (electromagnetic wave) to the object and acquires characteristic information of the object as image data. The characteristic information of the present invention is information of a characteristic value that is generated by using a reception signal obtained by receiving a photoacoustic wave and corresponds to each of a plurality of positions in the object.

The characteristic information acquired by the present invention is a value in which the absorptivity of light energy is reflected. For example, the generation source of the acoustic wave generated by light irradiation, an initial sound pressure in the object, and an absorption density and an absorption coefficient of light energy derived from the initial sound pressure can be referred to as "characteristic information based on light absorption". The characteristic information also includes concentration relating information of a substance constituting a tissue.

The concentration relating information includes a value relating to the concentration of a substance present in the object that is determined by using the characteristic information based on the light absorption corresponding to a plurality of wavelengths. Specifically, the concentration relating information includes an oxygen saturation, a value obtained by assigning the intensity of the absorption coefficient or the like as a weight to the oxygen saturation, a total hemoglobin concentration, an oxyhemoglobin concentration, and a deoxyhemoglobin concentration. Further, the concentration relating information may include a glucose concentration, a collagen concentration, a melanin concentration, and a volume fraction of fat or water. A two-dimensional or three-dimensional characteristic information distribution is obtained based on the concentration relating information at each position in the object. Distribution data can be generated as image data.

The acoustic wave mentioned in the present invention is typically a ultrasonic wave, and includes an elastic wave called a sound wave or the acoustic wave. An electrical signal converted from the acoustic wave by a probe or the like is also referred to as an acoustic signal. However, the description of the ultrasonic wave or the acoustic wave in the present description is not intended to limit the wavelength of the elastic wave thereof. The acoustic wave generated by the photoacoustic effect is referred to as a photoacoustic wave or a photo-ultrasonic wave. An electrical signal derived from the photoacoustic wave is also referred to as a photoacoustic signal.

Note that main purposes of the photoacoustic apparatus in the following embodiments are, for example, diagnosis of malignant tumors and vascular diseases of human beings and animals and a follow-up of chemotherapy. Therefore, the object includes part of a biological body, specifically includes regions of human beings and animals (breasts, organs, circulatory organs, digestive organs, bones, muscles, and fat), and they are assumed to be examination targets. In addition, a substance serving as the examination target includes hemoglobin and glucose, and also includes water, melanin, collagen, and lipid that exist in the body. Further, the substance may be any substance that has a characteristic light absorption spectrum such as a contrast medium such as an ICG (indocyanine green) administered to the inside of the body.

With regard to the concentration relating information, the oxygen saturation in flood is calculated within a range of an expected value of not less than 0% and not more than 100% (a value corresponding to a third numerical range) in general. However, when an initial sound pressure value or an absorption coefficient value of light obtained in the photoacoustic apparatus includes a calculation error caused by a noise or a reconstruction artifact, there are cases where a value that is not included in the expected value (0 to 100%) (unexpected value) is calculated as an oxygen saturation value. In these cases, the unexpected value is sometimes obtained at a position at which a measurement target (a blood vessel or the like) exists.

In the case where the unexpected value is included in the characteristic information distribution of the object acquired by the photoacoustic apparatus, there is a possibility that diagnostic performance by the photoacoustic apparatus is reduced. On the other hand, there is a possibility that the unexpected value is obtained even at the position of the measurement target, and hence there are cases where it is desired to display even an area of the unexpected value. To cope with this, in the present invention, the unexpected value is divided into an abnormal value (a value corresponding to a second numerical range) and a suspended value (a value corresponding to a first numerical range), and display methods of areas corresponding to the expected value, the abnormal value, and the suspended value are made different from each other. As a result, it is possible to prevent a reduction in diagnostic performance. Further, the third numerical range in which the oxygen saturation is not less than 0% and not more than 100% may also be set. A display control unit performs control capable of distinguishing the third numerical range, the first numerical range, and the second numerical range, whereby it is possible to further prevent the reduction in diagnostic performance.

First Embodiment (Overall Apparatus Configuration)

FIG. 1A is a schematic view showing a configuration of a photoacoustic apparatus of the present embodiment. The apparatus includes at least a light source 1, a probe 30 that includes a conversion element 3 that receives the photoacoustic wave, and a signal processing unit 40 that performs signal processing by using a reception signal output from the conversion element 3. In addition, the apparatus may also include an input unit 12 and a display unit 7.

Light output from the light source 1 is applied to an object 2 via a light propagation member (not shown) such as a fiber, a mirror, or a lens. Note that the light source 1 is preferably capable of applying a plurality of pulsed light beams having wavelengths that are different from each other to the object at different timings. The applied light propagates and diffuses in the object, and is absorbed by a light absorber in the object. As a result, the photoacoustic wave is generated from the light absorber by a photoacoustic effect. For example, when the light source is capable of applying light beams having two wavelengths, a first photoacoustic wave is generated by the light beam having a first wavelength, and a second photoacoustic wave is generated by the light beam having a second wavelength. The sound pressure of each photoacoustic wave at this point has a value corresponding to the light absorption spectrum of the light absorber. Each generated photoacoustic wave propagates in the object and reaches the conversion element 3. Note that the conversion element 3 is provided so as to acoustically match the object. It is preferable to use an acoustic matching material such as, e.g., water, gel, or castor oil.

Each of a plurality of the conversion elements 3 receives the photoacoustic wave, converts the received photoacoustic wave to a time-series reception signal, and outputs the reception signal. That is, the conversion element 3 outputs the time-series first reception signal by receiving the first photoacoustic wave, and outputs the time-series second reception signal by receiving the second photoacoustic wave. The output reception signal is input to the signal processing unit 40. The conversion element corresponds to a reception unit of the present invention.

To the signal processing unit 40, the reception signal is sequentially input on a per applied pulsed light beam. The signal processing unit 40 generates distributions such as the characteristic distribution and a concentration relating distribution based on the light absorption in the object. In addition, the signal processing unit 40 generates image data based on the generated distribution and causes the display unit 7 to display an image. Further, the signal processing unit 40 receives an input such as an area setting from a user (an operator such as a doctor or an engineer) via the input unit 12.

Note that, in the case where the photoacoustic apparatus is an apparatus that has a relatively small object as the examination target such as a photoacoustic microscope, the number of the conversion elements 3 of the probe 30 may be one. In addition, in the case where the photoacoustic apparatus is an apparatus that has a relatively large object such as a breast as the examination target, it is preferable to provide a plurality of the conversion elements 3 of the probe 30.

(Internal Configuration of Signal Processing Unit)

Next, a configuration in the signal processing unit 40 of the present embodiment will be described. The signal processing unit 40 includes a signal collection unit 9, a characteristic distribution acquisition unit 4, a concentration relating information acquisition unit 5, a display method setting unit 6, and a display control unit 8.

The signal collection unit 9 collects the time-series analog reception signal output from each of a plurality of the conversion elements 3 on a per channel basis, and performs signal processing such as amplification of the reception signal, AD conversion of the analog reception signal, and storage of a digitized reception signal. In addition, the signal collection unit 9 may perform signal correction processing.

The characteristic distribution acquisition unit 4 generates the characteristic distribution based on the light absorption in the object by using the reception signal output from the signal collection unit 9. Note that, in the following description, an example in which an absorption coefficient distribution is determined as the characteristic distribution based on the light absorption will be described. An absorption coefficient $\mu_a$ at a given position (coordinates (i, l, k)) in the object is determined by Expression (1).

[Math. 1]

$$P = \Gamma \cdot \mu_a \cdot \phi \qquad (1)$$

Herein, P represents the initial sound pressure (generated sound pressure) at the position (i, l, k), Γ represents the Gruneisen constant, and φ represents a light amount having reached the position (i, l, k).

Note that the initial sound pressure P at the position (i, l, k) on three-dimensional space coordinates is determined by image reconstruction to the reception signal of each channel output from the signal collection unit 9. At this point, a band correction filter of the probe may be used. To the image reconstruction, existing methods such as universal back projection (UBP) and filtered back projection (FBP) can be applied. In addition, delay and sum processing may also be used.

By performing the image reconstruction processing on each position in the object, it is possible to acquire an initial sound pressure distribution. The initial sound pressure distribution may be three-dimensional distribution data corresponding to a given area in the object (aggregate data of voxels) or may also be two-dimensional distribution data corresponding to one cross section thereof (aggregate data of pixels).

Note that, in the case of a light focusing photoacoustic microscope or an acoustic focusing photoacoustic microscope that uses a focusing probe, it is possible to generate the distribution data without performing the image reconstruction processing. Specifically, the probe 30 and a light irradiation spot are moved relative to the object 2 using a scanning mechanism (not shown), and the probe 30 receives the photoacoustic waves at a plurality of scanning positions. Subsequently, the characteristic distribution acquisition unit 4 performs envelope detection on the obtained reception signal with respect to temporal change, and then converts a time axis direction in a signal at each light pulse to a depth direction and plots the depth direction on spatial coordinates. By performing this process at each scanning position, the distribution data is obtained.

The characteristic distribution acquisition unit 4 determines the absorption coefficient distribution by using Expression (1) based on the initial sound pressure distribution determined in this manner. Note that the Gruneisen constant can be considered to be constant. The light amount Φ may be assumed to be constant in the object but, in order to determine the concentration relating information more accurately, it is better to determine a light amount distribution in the object. The light amount distribution can be acquired by calculation in which light propagation in the object is considered from the distribution of the applied light incident on the object. More simply, the light amount distribution may be obtained from model calculation corresponding to the type of the object. Thus, the characteristic distribution acquisition unit 4 determines the absorption coefficient distribution for each of a plurality of wavelengths emitted from a light irradiation unit (light source 1), and outputs the absorption coefficient distribution to the concentration relating information acquisition unit 5. The light irradiation unit (light source) corresponds to a light irradiation unit of the present invention.

The concentration relating information acquisition unit 5 generates the concentration relating distribution by using a plurality of the absorption coefficient distributions determined for the individual wavelengths output from the characteristic distribution acquisition unit 4. Note that, in the following description, an example in which an oxygen saturation distribution is determined as the concentration relating distribution will be described. At this point, the concentration relating information acquisition unit functions as a first acquisition unit of the present invention. A combination of the characteristic distribution acquisition unit and the concentration relating information acquisition unit can also be considered as the first acquisition unit of the present invention.

When it is assumed that the light absorption other than that of hemoglobin is negligibly low in each of a wavelength $\lambda_1$ and a wavelength $\lambda_2$, the absorption coefficients of the wavelength $\lambda_1$ and the wavelength $\lambda_2$ are represented as Expression (2) and Expression (3) by using the molar absorption coefficient of oxyhemoglobin and the molar absorption coefficient of deoxyhemoglobin.

[Math. 2]

$$\mu_a(\lambda_1) = \varepsilon_{ox}(\lambda_1) C_{ox} + \varepsilon_{de}(\lambda_1) C_{de} \quad (2)$$

$$\mu_a(\lambda_2) = \varepsilon_{ox}(\lambda_2) C_{ox} + \varepsilon_{de}(\lambda_2) C_{de} \quad (3)$$

Herein, $\mu_a(\lambda_1)$ represents the absorption coefficient of light having the wavelength $\lambda_1$ at a position (i, j, k), $\mu_a(\lambda_2)$ represents the absorption coefficient of light having the wavelength $\lambda_2$ at the position (i, j, k), and the unit thereof is [mm$^{-1}$]. $C_{ox}$ represents the amount of oxyhemoglobin [mol], and $C_{de}$ represents the amount of deoxyhemoglobin [mol]. Both of them are assumed to represent values at positions (i, j, k).

$\varepsilon_{ox}(\lambda_1)$ and $\varepsilon_{de}(\lambda_1)$ represent the molar absorption coefficients [mm$^{-1}$mol$^{-1}$] of oxyhemoglobin and deoxyhemoglobin in the wavelength $\lambda_1$. $\varepsilon_{ox}(\lambda_2)$ and $\varepsilon_{de}(\lambda_2)$ represent the molar absorption coefficients [mm$^{-1}$mol$^{-1}$] of oxyhemoglobin and deoxyhemoglobin in the wavelength $\lambda_2$. $\varepsilon_{ox}(\lambda_1)$, $\varepsilon_{de}(\lambda_1)$, $\varepsilon_{ox}(\lambda_2)$, and $\varepsilon_{de}(\lambda_2)$ can be acquired in advance by using measurements and literature values. Therefore, $C_{ox}$ and $C_{de}$ are determined by solving simultaneous equations of Expression (2) and Expression (3) by using the molar light absorption coefficients and $\mu_a(\lambda_1)$ and $\mu_a(\lambda_2)$. In the case where the number of used wavelengths is large, the least square method may be appropriately used.

As shown in Expression (4), an oxygen saturation $SO_2$ is defined by the ratio of oxyhemoglobin in total hemoglobin. Therefore, the oxygen saturation $SO_2$ is represented by Expression (5) based on Expressions (2), (3), and (4). Therefore, the concentration relating information acquisition unit 5 can acquire the oxygen saturation $SO_2$ at the position (i, j, k) based on the molar light absorption coefficients and $\mu_a(\lambda_1)$ and $\mu_a(\lambda_2)$ by using Expression (5).

[Math. 3]

$$SO_2 = \frac{C_{ox}}{C_{ox} + C_{de}} \quad (4)$$

$$SO_2 = \frac{\frac{\mu_a(\lambda_2)}{\mu_a(\lambda_1)} \cdot \varepsilon_{de}(\lambda_1) - \varepsilon_{de}(\lambda_2)}{(\varepsilon_{ox}(\lambda_2) - \varepsilon_{de}(\lambda_2)) - \frac{\mu_a(\lambda_2)}{\mu_a(\lambda_1)} \cdot (\varepsilon_{ox}(\lambda_1) - \varepsilon_{de}(\lambda_1))} \quad (5)$$

By performing such processing on each position, it is possible to acquire the oxygen saturation distribution inside the object. FIGS. 3A to 3E show examples of a display screen in the case where the oxygen saturation distribution is obtained from the absorption coefficient distribution of the wavelength $\lambda_1$ and the absorption coefficient distribution of the wavelength $\lambda_2$. A reference numeral 301 (FIG. 3A) indicates an image of the absorption coefficient distribution of the wavelength $\lambda_1$, a reference numeral 302 (FIG. 3B) indicates an image of the absorption coefficient distribution of the wavelength $\lambda_2$, and a reference numeral 303 (FIG. 3C) indicates an image of the oxygen saturation distribution. The image 303 is represented with a range in which the maximum value of the calculated value of the oxygen saturation can be displayed. That is, the image 303 represents the distribution of the oxygen saturation having the calculated values of 0% to 150%. The oxygen saturation distribution may be three-dimensional distribution data corresponding to a given area in the object (aggregate data of voxels) or may also be two-dimensional distribution data corresponding to one cross section thereof (aggregate data of pixels).

In FIGS. 3A to 3E, the oxygen saturation value in an area in which the absorber does no exit is set to 0% for the sake of convenience. The oxygen saturation distribution is obtained by using the ratio of the absorption coefficient distribution, and the oxygen saturation distribution is properly determined when the absorption coefficient distributions in a plurality of the wavelengths are relatively correct. Therefore, the absorption coefficient distribution does not need to be accurately determined as an absolute value.

On the other hand, a reference numeral 304 (FIG. 3D) indicates an image that displays an area in which the oxygen saturation is not less than 0% and not more than 100% after processing that emphasizes the area of a blood vessel is performed on the oxygen saturation distribution image 303. That is, the image 304 is a comparative example to the present invention. When attention is paid to an upper right portion of the image 304, a blood vessel image having a value exceeding the display range is not present.

In addition, a reference numeral 305 (FIG. 3E) indicates an image that displays an area in which the oxygen saturation is not less than 0% and not more than 120% after processing that emphasizes the area of the blood vessel is performed on the oxygen saturation distribution image 303. When attention is paid to the upper right portion of the image 305, the oxygen saturation distribution of the blood vessel that has disappeared due to an error by a noise in the image 304 is displayed. Note that, in each of the images 304 and 305, in order to increase viewability, the processing that emphasizes the portion of the blood vessel as compared with the other portions is performed. Herein, a portion in which the absorption coefficient distribution shown in the image 301 or 302 had a value higher than a predetermined threshold value was determined as the blood vessel. In addition, the color of an area determined as an area without the blood vessel was made identical with a background color. The display control unit may extract a spatial distribution of the blood vessel portion and cause the display unit to display the spatial distribution of the blood vessel portion. At this point, by assigning the absorption coefficient to a lightness, clarification can be performed.

Figure 4A:
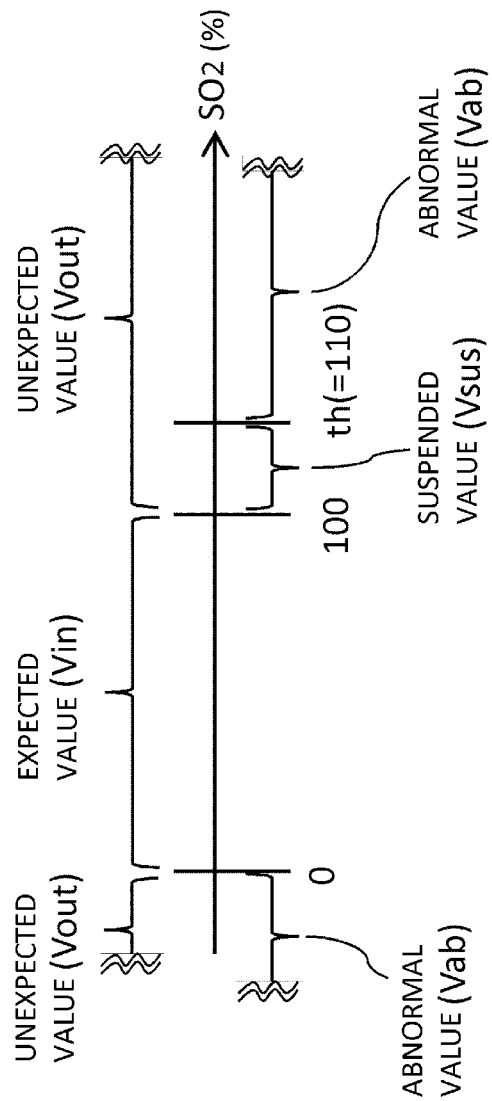
FIG. 4A and FIG. 4B are views for explaining a division of each value range.

The display method setting unit 6 sets the image display method for the oxygen saturation distribution determined in the concentration relating information acquisition unit 5. At this point, setting based on input information from the input unit 12 may be performed. A value at each position of the concentration relating information distribution will be described by using FIG. 4A.

An "expected value ($V_{in}$)" denotes a range of a value that is normally expected based on a measurement system (an apparatus configuration and a calculation principle) of the present invention. The oxygen saturation or the substance concentration is expected to fall within a range of the expected value of not less than 0% and not more than 100% in the calculation principle. The expected value is considered to be the value range of the ideal concentration relating information distribution derived by the ideal measurement system, and hence the expected value may also be referred to as an ideal value. Conversely, a value of less than 0% or more than 100% is an "unexpected value (Vout)".

Herein, the unexpected value includes an "abnormal value (Vab)" and a "suspended value (Vsus)". An abnormal value area is an object area in which an influence by the noise or the like is increased so that a significant value is not obtained in a portion that is not the measurement target obviously (e.g., a biological tissue other than the blood vessel). In the drawing, when the value is more than 110%, the value is the abnormal value. On the other hand, the suspended value denotes a range of a value range of a value that might be a value obtained from an area that is not the measurement target but might also be a value obtained from the measurement target (the blood vessel or hemoglobin) and having deviated slightly from the expected value due to an error in a calculation process or the like. In the drawing, when the value is more than 100% and is not more than 110%, the value is the suspended value.

The position indicative of the suspended value is permitted to be displayed without being subjected to masking or the like, and hence the suspended value may also be referred to a permitted value. In addition, the value range in which the expected value and the suspended value are combined is a range in which the value might be a normal value, and hence these values may be referred to as the normal values.

A reason for providing the suspended value will be described. On the absorption coefficient distribution calculated in the apparatus, errors caused by the noise, the reconstruction artifact, and a background optical constant are superimposed. Accordingly, there are cases where the calculated oxygen saturation deviates from the expected value. Conventionally, with regard to the position in the object at which the oxygen saturation has the unexpected value, processing such as removal of the value by mask processing, displaying using the same color as the background color, and giving the same color as that in the case where the value is 100% to the position (the value is rounded to 100%) has been performed. However, with such processing, a user cannot determine a portion in which the noise or the reconstruction artifact occurs. In addition, there is a possibility that an area in which the unexpected value is calculated due to the calculation error of the oxygen saturation falls within the expected value area with the ideal measurement system. However, with the above-described conventional processing, such an area is uniformly determined as an abnormal value area.

However, according to the display of the present invention, the suspended value is not mixed with the expected value or the abnormal value, and the user can recognize the suspended value area. As a result, it is possible to determine whether or not the suspended value area is the measurement target by a visual check by the user or image processing such as pattern recognition, and hence more accurate diagnosis is performed. The same display system as that for the expected value may be applied to the area that is found as the expected value as the result of the determination. At this point, the value exceeding 100% may be rounded to 100%. That is, in the case where the value of the oxygen saturation calculated at a given position corresponds to the suspended value that exceeds 100%, the value of the oxygen saturation at the position may be displayed as 100%. In this case as well, the display is performed such that the calculated value of the oxygen saturation can be distinguished from the abnormal value that exceeds 100%. For example, it is possible to display the image of the oxygen saturation distribution such that brightness is given to the position with the suspended value that exceeds 100% and brightness is not given to the position with the abnormal value that exceeds 100% (the position is not displayed). Alternatively, when the maximum oxygen saturation value is, e.g., 108%, the value range of 0 to 108% may be assigned to a hue, and the display may be performed again. In addition, the area that is found as the abnormal value may be re-displayed similarly to the other abnormal values. Such re-display processing may be automatically performed based on the determination result, or may also be performed based on an instruction from the user.

The display control unit may cause the display unit to display different numerical ranges (e.g., the first numerical range and the second numerical range) with different color scales. At this point, the color scale in which a color is continuously changed from a color assigned in the case where the oxygen saturation is 100% may be assigned to the first numerical range. Further, at this point, the color scale may be assigned such that a chroma is continuously reduced while the oxygen saturation reaches a first value from 100% in the first numerical range. Furthermore, at this point, the display in which the chroma is set to 0 may be performed in the case where the oxygen saturation has the first value and in the case where the oxygen saturation is in the second numerical range. In addition, the hue may be fixed in the first numerical range.

Additionally, the display control unit may assign a single color to the second numerical range. Examples of the single color include white and black.

In addition, the display control unit may cause one of the first numerical range and the second numerical range to flash.

Further, the display control unit may cause the display unit to display an annotation that provides notification of at least one of the area of the first numerical range and the area of the second numerical range.

Note that the error in the calculation process denotes a calculation error occurring at each position of the concentration relating information distribution. Examples thereof include the error by the noise or the reconstruction artifact and the error by the background optical constant. The background optical constant includes an average absorption coefficient and an equivalent scattering coefficient of the object.

The expected value of the oxygen saturation distribution is in a range of ($0 \leq V_{in} \leq 100\%$). The value range of the suspended value is obtained by adding a value corresponding to the calculation error to the value range of the estimated value. Consequently, when it is assumed that the calculation error of the concentration relating information distribution is ±10%, the suspended value is in a range of ($-10 \leq V_{sus} < 0\%$) and ($100 < V_{sus} \leq 110\%$). However, in the present embodiment, the oxygen saturation value of less than 0% is not considered to be the suspended value but is considered to be the abnormal value uniformly. This is based on the fact that a certain amount of oxyhemoglobin is included in venous blood according to an empirical rule, and hence the oxygen saturation in blood is less likely to have a value in the vicinity of 0%. Note that a detailed method for determining the calculation error at each position of the concentration relating information distribution will be described later.

Subsequently, the image display method for each value range in the present embodiment will be described. Typically, there is a method in which different color maps are used in different value ranges. For example, there is a method in which a hue display in which 0 to 100% is assigned to a color spectrum is performed for the expected value, the suspended value is displayed by using the single color and change of the lightness, and the abnormal value is not displayed. In addition, there is a method in which the pattern of one of the expected value area and the suspended value area is set to the pattern different from that of the other one thereof. Further, there is a method in which one of them is caused to flash and displayed. As long as the individual value ranges can be presented to the user so as to be distinguishable from each other, any method may be used. In addition, in these displays, the expected value and the suspended value may be handled collectively, and put in contrast with the abnormal value.

The apparatus of the present embodiment is capable of distinguishing at least one of the expected value, the suspended value, and the abnormal value in the concentration relating information distribution from the other values, and displaying it. As a result, determination of the portion of the oxygen saturation distribution in which the noise or the artifact occurs is helped.

The display control unit 8 generates image data to be displayed in the display unit 7 based on the distribution data such as the absorption coefficient distribution generated by the characteristic distribution acquisition unit 4 and the oxygen saturation distribution generated by the concentration relating information acquisition unit 5. Specifically, the display control unit 8 performs image processing such as brightness conversion, distortion correction, and logarithmic compression based on the distribution data. Further, the display control unit 8 performs display control such as arranging and displaying various display items together with the distribution data. The display control unit corresponds to a display control unit of the present invention. The display unit corresponds to a display unit of the present invention.

(Processing Flow of Signal Processing Unit)

Next, with reference to FIG. 2, a processing flow of the signal processing unit 40 will be described. This flow is started in a state in which the reception signal is sequentially input to the signal collection unit 9 in the signal processing unit 40 from the probe on a per wavelength of the applied light basis, and processing such as AD conversion and amplification is performed in the signal collection unit 9.

In Step S101, the characteristic distribution acquisition unit 4 acquires the absorption coefficient distribution in the wavelength $\lambda_1$ by using the reception signal of light having the wavelength $\lambda_1$, and acquires the absorption coefficient distribution in the wavelength $\lambda_2$ by using the reception signal of light having the wavelength $\lambda_2$.

In Step S102, the concentration relating information acquisition unit 5 generates the oxygen saturation distribution in the target area by using the absorption coefficient distribution in the wavelength $\lambda_1$ and the absorption coefficient distribution in the wavelength $\lambda_2$. Note that a partial area in the absorption coefficient distribution may be set as the target area by an area setting unit 13, and the same range as that of the absorption coefficient distribution may also be set as the target area. The range specified by the user via the input unit 12 may be set as the target area.

In Step S103, the display method setting unit 6 sets the range of each value range for the oxygen saturation distribution determined by the concentration relating information acquisition unit 5 and the color map for each value range. Herein, it is assumed that the range of each value range and the color map are preset in the apparatus. These set values are stored in a storage apparatus (not shown) in or outside the signal processing unit. The instruction from the user may also be received via the input unit 12.

In the present flow, the expected value of the oxygen saturation distribution is assumed to satisfy $(0 \leq V_{in} \leq 100\%)$, and the suspended value is assumed to satisfy $(100 < V_{sus} \leq 110\%)$. Herein, the suspended value is not provided on the side of the value less than 0% for the purpose of performing simple processing based on the fact that the oxygen saturation is less likely to have a value in the vicinity of 0% according to the empirical rule. Therefore, a value less than 0% or more than 110% is the abnormal value. Note that the range of the suspended value can be arbitrarily set according to measurement accuracy and the target error range.

In Step S104, the color map for each of the expected value and the suspended value is set. The color map set in an HSV color space is converted to the color map in an RGB color space, and the color map in the RGB color space is used. The HSV color space is a color space that includes three color components of a hue (Hue), a saturation (Saturation Chroma), and a value (Value·Lightness·Brightness), and is also referred to as an HSL color space or an HSB color space. The hue (H) represents the kind of color (red, blue, yellow or the like), and has a range of 0 to 360. Herein, red is 0, green is 120, blue is 240, and red appears as 360, and all hues are represented in this manner. The saturation (S) represents vividness of color, and has a range of 0 to 100%. As the saturation lowers, gray becomes conspicuous. The value (V) represents brightness of color, and has a range of 0 to 100%. On the other hand, the RGB color space is a color space represented by using three colors of red (Red), green (Green), and blue (Blue).

In the range in which the oxygen saturation has the expected value, the hues (H) from blue (240) to red (0) via green (120) are caused to correspond to 0% to 100% of the oxygen saturation values. Herein, the saturation (S) is set to 100%. Next, in the range of the suspended value among the unexpected values, the hue remains red (0), and the saturation (S) is reduced from 100% to 0%. Further, in the range of the abnormal value among the unexpected values, the range in which the oxygen saturation value is not more than 0% is set to blue (240), and the range in which the oxygen saturation value is not less than 110% is set to white. In the case of either color map, an absorption coefficient intensity normalized to 100% is substituted for the value (V), and the value is changed according to the magnitude of the absorption coefficient intensity. Finally, the color map in the HSV color space for the set oxygen saturation value is converted to the color map in the RGB color space, and the color space in the RGB color space is stored. With this arrangement, it is possible to provide different display rules for different value ranges of the oxygen saturation value such that the display rules can be distinguished from each other.

In Step S105, the display control unit 8 generates the image data of the oxygen saturation distribution calculated in the concentration relating information acquisition unit 5 based on the color map set in the display method setting unit 6, and displays the image data in the display unit 7.

Thus, in the present embodiment, it becomes possible to determine the abnormal value area by dividing the value range into the value ranges of the expected value, the suspended value, and the abnormal value based on the calculation error included in the oxygen saturation distribution as the imaging target, and changing the display method according to the value range.

<Modification 1: Kind of Information to be Displayed>

Note that the concentration relating distribution is not limited to the oxygen saturation distribution. The concentration relating distribution may be any distribution as long as the distribution is the distribution of a value relating to the concentration of a substance determined by using the characteristic distribution based on the light absorption of a plurality of wavelengths. For example, the concentration relating distribution may be the distribution of a value obtained by assigning a weight to the oxygen saturation, a total hemoglobin concentration, an oxyhemoglobin concentration, a deoxyhemoglobin concentration, a glucose concentration, a collagen concentration, a melanin concentration, a volume fraction of fat or water, a body fat percentage or the like.

Further, the target to which the display method of the present invention is applied may be a presence amount of any biological substance or a characteristic value indicative of the characteristic of a biological component instead of the concentration relating distribution. In other wards, the present invention is applicable in the case where any value obtained by the photoacoustic apparatus is divided into the expected value (ideal value), the suspended value (permitted value), and the abnormal value. For example, consideration is given to the case where it is assumed that the concentration of a given component is in a range of ($D_a$ to $D_b$) based on characteristics of the calculation method, and an error of ±15% can occur due to the characteristics of the measurement method. At this point, according to the approach of the present invention, the image display is performed by using the display method different from that for the expected value in a range in which the value corresponds to the expected value±15%.

In addition, in the example described above, the characteristic distribution acquisition unit 4 has acquired the absorption coefficient distribution as the characteristic distribution based on the light absorption, but the present embodiment is not limited thereto, and the characteristic distribution may also be the sound pressure distribution (typically the initial sound pressure distribution) or a light energy absorption density distribution. For example, since $\mu_a$ is represented by $P/(\Gamma \cdot \varphi)$ from Expression (1), it is possible to directly calculate the oxygen saturation from the initial sound pressure by replacing $\mu_a$ in Expression (5) with $P/(\Gamma \cdot \Phi)$. That is, even when the characteristic distribution acquisition unit 4 does not determine the absorption coefficient distribution temporarily after having determined the initial sound pressure distribution, the concentration relating information acquisition unit 5 can directly determine the oxygen saturation distribution from data on the initial sound pressure distribution.

The measurement target area is not limited to the blood portion in the blood vessel. The measurement target area may also be a vessel wall, a lymphatic vessel, a muscle tissue, a mammary gland tissue, a fat tissue, a substance injected from the outside such as a contrast medium or a molecular target drug, or an aggregate thereof.

<Modification 2: Display Method>

Ranges of the expected value, the suspended value, and the abnormal value, and predetermined threshold values (th) for determining them are not limited to those described above. In addition, each value range may be changed according to the specification of an operator or apparatus conditions. Further, the use of the display method in each value range is arbitrarily determined.

For example, there is a method in which a continuous color map is used in the expected value and the suspended value. In addition, there is a method in which the color map of the abnormal value is made identical with the background color of the image, and there is a method in which the saturation (S) of the color map of the abnormal value is set to 0, the value (V) is set to 0, or the hue (H) is set to 0. Typically, the abnormal value area is displayed in black. In addition, the hue (H) and the saturation of the color map to the change of the oxygen saturation value are assumed to be linearly changed, but may also be changed nonlinearly as long as the display is a proper display for showing the change of the oxygen saturation. In addition, recognizability may be enhanced by using a color that is not used by color maps of the other value ranges as the color map of the abnormal value.

Figure 4B:
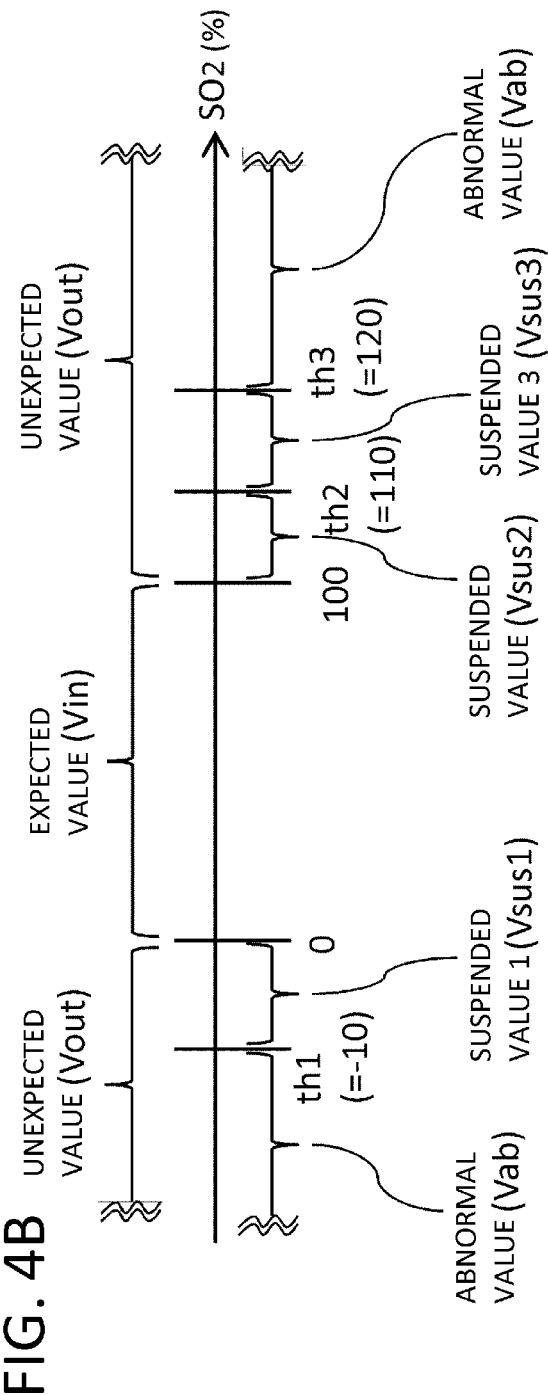

As shown as a suspended value 2 and a suspended value 3 in FIG. 4B, the display method may be changed according to the degree of deviation from the expected value. In addition, in the case where the characteristic value is less than 0, a suspended value 1 may be provided. These set values may be pre-stored in a storage apparatus, or the instruction from the user may be received via the input unit 12. Further, the range of each value range, the threshold value, the display method for each value range and the like may be switched by the user via the input unit 12 during the display of the image.

<Modification 3: Blood Vessel Emphasis Processing>

In the case where the present invention is applied to the display of the oxygen saturation distribution, it is important to determine the position of presence of blood (i.e., the position of the vessel vessel) with excellent accuracy and clearly present the position to the user. To cope with this, it is preferable to combine the display method of the present invention with an emphasis technique or a trimming technique of the blood vessel position.

As the blood vessel emphasis technique, for example, there is a method in which a position at which the intensity of a signal component considered to be derived from hemoglobin based on the absorption coefficient distribution is high is considered to be the position of the blood vessel, and the position is emphasized and displayed as compared with a position at which the intensity thereof is low. In addition, as the technique for determining the blood vessel position, there is a method in which the blood vessel position is determined based on a photoacoustic image taken preliminarily, and there is a method in which a blood vessel position determination unit for measurement by other modalities (a camera, an infrared light camera, an ultrasonic echo apparatus or the like) is provided. A clear display for the user is realized by a blood vessel trimming display or a blood vessel emphasis display based on the determined blood vessel position. Conversely, the probability of presence of the blood vessel in a portion in which the oxygen saturation has the abnormal value is low, and hence such an area may be set as a target of deletion by trimming processing.

<Preferable Configuration of Apparatus>

Next, specific examples of the individual constituent units of the present embodiment will be described.

(Light Source 1)

The light source 1 is preferably a pulsed light source that emits pulsed light in the order of nanoseconds to microseconds. A preferable pulse width in the emission is about not less than 1 nanosecond and not more than 100 nanoseconds. In addition, the wavelength of light is preferably in a range of not less than 400 nm and not more than 1600 nm. When a deep portion of a biological body is imaged, a wavelength band that is called "the window of a biological body" (a wavelength band that has small absorption in the background tissue of the biological body) is preferable. Specifically, the wavelength band is not less than 700 nm and not more than 1100 nm. On the other hand, when the blood vessel in the vicinity of the surface of the biological body is imaged with high resolution, a visible light region is preferable. However, it is also possible to use terahertz wave, microwave, and radio wave regions.

As the specific light source 1, a laser apparatus is preferable. In the case where the substance concentration is determined by using light beams having a plurality of wavelengths, a wavelength tunable laser is used. In addition, it is also possible to use a plurality of lasers that emit light beams having different wavelengths while switching between the lasers. As the laser, it is possible to use various lasers such as a solid state laser, a gas laser, a dye laser, and a semiconductor laser. In particular, a pulsed laser such as an Nd:YAG laser or an alexandrite laser is preferable. In addition, a Ti:sa laser that uses Nd:YAG laser light as excitation light and an OPO (Optical Parametric Oscillators) laser may also be used. It is also possible to use a flash lamp, a light-emitting diode or the like as the light source.

The pulsed light output from the light source 1 is guided to the object by a member (optical member) that propagates light such as an optical fiber, a lens, a mirror, or a diffuser. In addition, when the pulsed light is guided, it is possible to change the spot shape or the light density of the pulsed light by using these optical members.

(Probe 30)

The probe 30 includes one or more conversion elements 3. As the conversion element 3, there are a piezoelectric element that uses a piezoelectricity of lead zirconate titanate (PZT) or the like, a conversion element that uses resonance of light, and a capacitive conversion element such as a CMUT. In addition, any conversion element may be used as long as the conversion element is capable of receiving the acoustic wave and converting the acoustic wave to the electrical signal. In the case where a plurality of the conversion elements 3 are provided, the conversion elements 3 are preferably disposed so as to be arranged on a plane or curved plane that is called 1D array, 1.5D array, 1.75D array, or 2D array.

The probe 30 may also be configured so as to mechanically move relative to the object, and the probe 30 may also be a hand-held probe 30 that is held and moved by the user. In the case of the photoacoustic microscope, the probe 30 is preferably a focusing probe, and the probe 30 preferably moves mechanically along the surface of the object. In addition, the irradiation position of the applied light and the probe 30 preferably move in synchronization with each other. In the probe 30, an amplifier that amplifies the analog signal output from the conversion element 3 may be provided. In the case where mechanical scanning of the probe is performed, stability of measurement may be improved by providing a plate-like holding member that presses and holds the object or a holding member consisting of two plates that hold the object therebetween.

In addition, the probe 30 in which a plurality of the conversion elements 3 are mounted to an inner wall of a supporter in the shape of a semi-sphere, a spherical crown, a bowl, a cup or the like may be used. In the case of this probe 30, it is possible to form an area in which directions of a plurality of the conversion elements in which reception sensitivity is high are concentrated (high-sensitivity area) to improve a resolution of an image. In the case where such a probe is used, it is preferable to hold the object using a cup-shaped holding member that transmits light and the acoustic wave.

(Display Unit 7)

As the display unit 7, it is possible to use displays such as an LCD (Liquid Crystal Display), a CRT (Cathode Ray Tube), and an organic EL display. Note that, instead of adopting the configuration in which the object information acquisition apparatus of the present embodiment includes the display unit 7, the display unit 7 may also be prepared separately and connected to the object information acquisition apparatus.

(Signal Processing Unit 40)

In the signal collection unit 9, it is possible to use a circuit that is generally called a DAS (Data Acquisition System). Specifically, the signal collection unit 9 includes an amplifier that amplifies the reception signal, an AD converter that digitizes the analog reception signal, and a memory that stores the reception signal such as a FIFO or a RAM.

In the characteristic distribution acquisition unit 4, the concentration relating information acquisition unit 5, and the display method setting unit 6, it is possible to use processors such as a CPU, an MPU, and a GPU (Graphics Processing Unit). In addition, an arithmetic circuit such as an FPGA (Field Programmable Gate Array) chip or the like may also be used. Note that each of the characteristic distribution acquisition unit 4 and the concentration relating information acquisition unit 5 may be configured by a plurality of processors and arithmetic circuits instead of being configured by one processor and one arithmetic circuit.

In addition, each of the characteristic distribution acquisition unit 4, the concentration relating information acquisition unit 5, and the display method setting unit 6 may include a memory that stores the reception signal output from the signal collection unit 9. The memory is typically configured by a storage medium such as a ROM, a RAM, or a hard disk. Note that the memory may be configured by a plurality of storage media instead of being configured by one storage medium.

Similarly, the display method setting unit 6 can be configured by a processor such as a CPU or a GPU and a circuit such as an FPGA chip or by combining a plurality of processors and circuits. In addition, the display method setting unit 6 may include a memory that stores the reception signal, distribution data, display image data, and various measurement parameters. The memory is typically configured by storage media such as one or more ROMs, RAMs, and hard disks.

FIG. 1B is a schematic view showing a relationship between one specific example of the signal processing unit 40 and external apparatuses. The signal processing unit 40 includes a DAS 201, a memory 202, a CPU 203, and a GPU 204. The DAS 201 performs one function of the signal collection unit 9 in the present embodiment. The digital signal transferred from the DAS 201 is stored in the memory 202.

The CPU 203 performs part of functions of the characteristic distribution acquisition unit 4, the concentration relating information acquisition unit 5, the display control unit 8, and the display method setting unit 6 in the present embodiment. Specifically, the CPU 203 controls individual configuration blocks via a system bus 200. In addition, the CPU 203 can perform signal processing such as summation and correction on the digital signal stored in the memory 202. Further, the CPU 203 writes the digital signal after the signal processing into the memory 202 again, and the digital signal is used for the generation of the distribution data by the GPU 204.

The GPU 204 performs part of functions of the characteristic distribution acquisition unit 4, the concentration relating information acquisition unit 5, the display control unit 8, and the display method setting unit 6 in the present embodiment. Specifically, the GPU 204 generates the distribution data by using the digital signal that has been subjected to the signal processing and written into the memory 202 by the CPU 203. In addition, the GPU 204 can generate image data by applying various image processing such as brightness conversion, distortion correction, and cutting out of a target area to the generated distribution data. Note that the similar processing can be performed also by the CPU 203. The concentration relating information calculation unit and the display method setting unit are considered to correspond to a determination unit of the present invention. However, the display method setting unit and the display control unit may be considered to correspond to the display control unit of the present invention by combining the partial function of the display method setting unit and the function of the display control unit. In addition, in the signal processing unit 40, a plurality of predetermined modules among programs that operate in a single information processing apparatus or a plurality of information processing apparatuses that cooperate with each other may be considered to correspond to a determination unit and the display control unit of the present invention.

(Input Unit 12)

The input unit 12 is an interface for receiving various instructions such as a numerical range specification, an area specification, and switching of the display method from the user, and transmitting them to the signal processing unit. As the input unit, it is possible to use a mouse, a keyboard, a trackball, a touch pad, a touch pen, a touch-panel display, a command line input apparatus, a voice input apparatus and the like. The input unit corresponds to a second acquisition unit of the present invention.

Example 1

Hereinbelow, a more specific example will be described. In the present Example, a phantom that simulates a breast is used as the object, light is applied to the object through a holding member made of polymethyl pentene that holds the object, and the probe 30 receives the photoacoustic wave through the holding member. The probe 30 is a 2D array probe having a plurality of conversion elements of a frequency band of 1 MHz±40%.

In the present Example, first, pulsed light having a wavelength of 797 nm is applied to the object from the light source 1, and the photoacoustic wave is received by the probe 30. The signal processing unit 40 performs the image reconstruction by using the universal back projection based on the reception signal after amplification and AD conversion are performed. Subsequently, the absorption coefficient distribution is generated by using the determined initial sound pressure distribution and light amount distribution, and the Gruneisen constant. The value of the absorption coefficient distribution is in the form of voxel data, and one voxel is a cube 0.25 mm on a side. The obtained absorption coefficient distribution is 200 voxels in length, 200 voxels in width, and 200 voxels in height.

Next, pulsed light having a wavelength of 756 nm is applied to the object from the light source 1, and the photoacoustic wave is received by the probe 30. The signal processing unit 40 performs the image reconstruction by using the universal back projection based on the reception signal obtained by the reception. Subsequently, the signal processing unit 40 generates the absorption coefficient distribution by using the determined initial sound pressure distribution and light amount distribution, and the Gruneisen constant.

The signal processing unit 40 calculates the oxygen saturation distribution based on the absorption coefficient distribution of 756 nm and the absorption coefficient distribution of 797 nm. The calculation of the oxygen saturation is performed by using the corresponding voxels of the individual wavelengths, and the oxygen saturation distribution is 200 voxels in length, 200 voxels in width, and 200 voxels in height similarly to the absorption coefficient distribution.

The color map for displaying the oxygen saturation value that uses the hue (H) and the saturation (S) will be described. The low abnormal value (less than 0%) is displayed in blue, the expected value (0% to 100%) is displayed in blue to red via green, the suspended value (100 to 110%) id displayed in red to white, and the high abnormal value (a value more than 110%) is displayed in white. A weight obtained from the intensity of the absorption coefficient distribution is substituted for the value (V). At this point, the value of the absorption coefficient is normalized with a value set by an operator, and the weight is thereby calculated. With this, an effect that an area that is considered to be the blood vessel and an area that is considered to include much hemoglobin are emphasized and displayed is obtained.

A method for displaying three-dimensional voxel data as a plurality of two-dimensional images corresponding to a plurality of slices in a height direction will be described. First, each voxel is scanned in the height direction, the oxygen saturation value in the voxel having the largest weight of the absorption coefficient value is selected from among the oxygen saturation values in the scanned voxels, and is displayed as the image. However, the display method is not limited thereto, and it is possible to use various existing methods for displaying the three-dimensional voxel data two-dimensionally.

The color map expressed in the HSV color space is converted to the color map in the RGB color space at the time of the display. The conversion of the color space depends on display software to be used. When the software is capable of displaying with the color map in the HSV color space, the HSV display is performed. In addition, the color map in the HSV color space may be converted to the color map in the RGB color space, an sRGB color space, an RGBA color space, a CMY color space, a CMYK color space, a CMK color space, an HLS color space or the like.

Herein, the suspended value was set to 100 to 110%. However, in the case where it is theoretically known that the calculation error of the oxygen saturation is about ±10% in advance, the value range of the suspended value may be set to 100 to 115% that includes a margin. In this case, it is possible to determine that an area in which the value is more than 110% is inevitably the abnormal value area. Alternatively, as shown in FIG. 4B, a plurality of the suspended values may be provided according to the degree of deviation from the expected value, and the suspended values may be displayed by using different rules.

According to the present Example, even in the case where the calculation error caused by the noise, the reconstruction artifact, or the background optical constant is included in the absorption coefficient distribution, and the concentration relating information such as the oxygen saturation thereby has the unexpected value, it is possible to display the image such that recognition by the user is facilitated.

Second Embodiment

The apparatus configuration and the processing flow in a second embodiment will be described with a focus on portions different from those in the first embodiment.

In the object information acquisition apparatus of the present embodiment, the display method for each value range of the concentration relating information distribution set by the display method setting unit 6 is different. Specifically, the expected value area, the suspended value area, and the abnormal value area are distinguished from each other and displayed by using flashing of color and a texture image. Different displays may be used in the three different areas. In addition, two areas (e.g., the expected value area and the suspended value area) may be combined, and displayed so as to be different from the abnormal value area.

Figure 2:
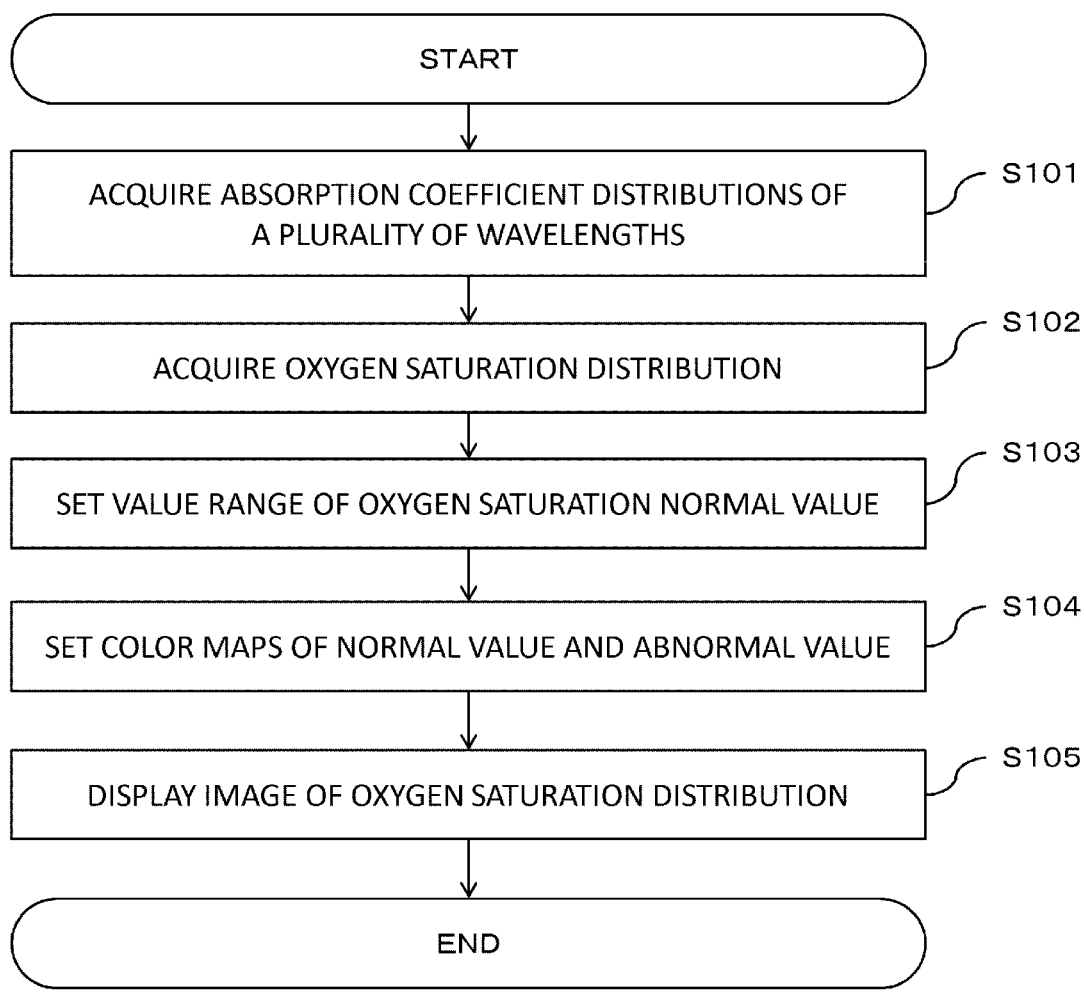
FIG. 2 is a flowchart showing an operation of a signal processing unit.
Figure 3A:
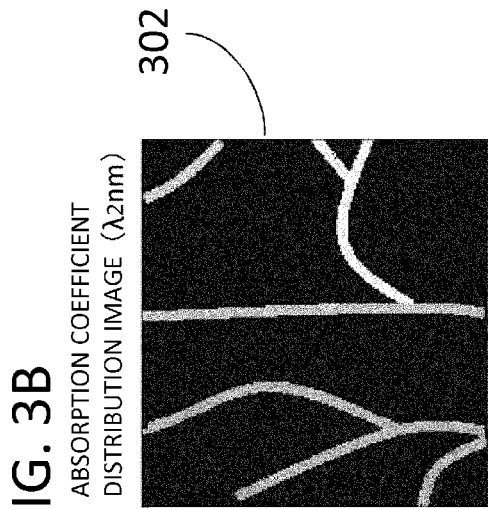
FIG. 3A to FIG. 3E are schematic views showing examples of a display screen.
Figure 3B:
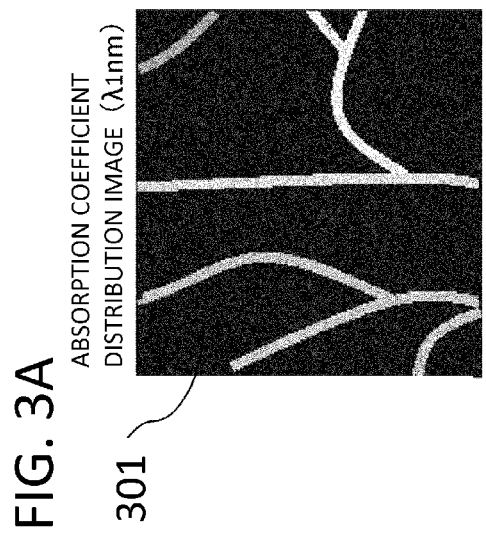
Figure 3C:
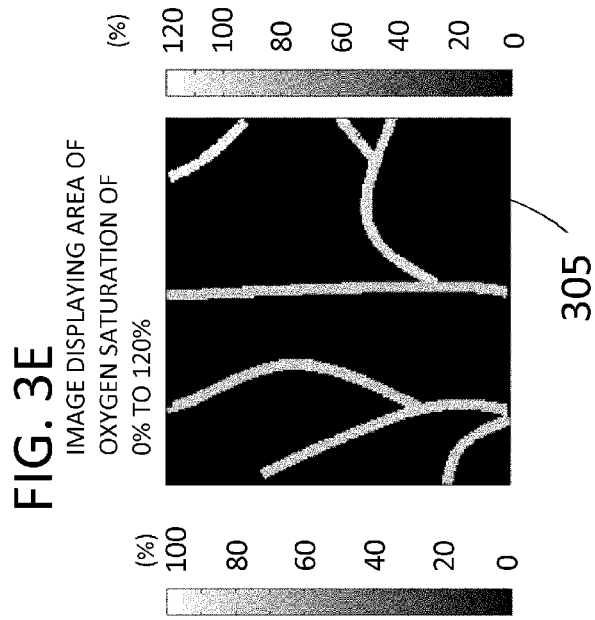
Figure 3D:
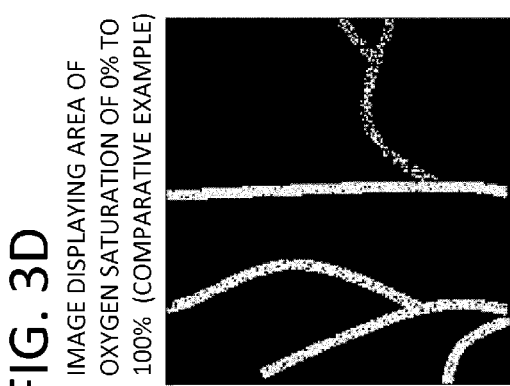
Figure 3E:
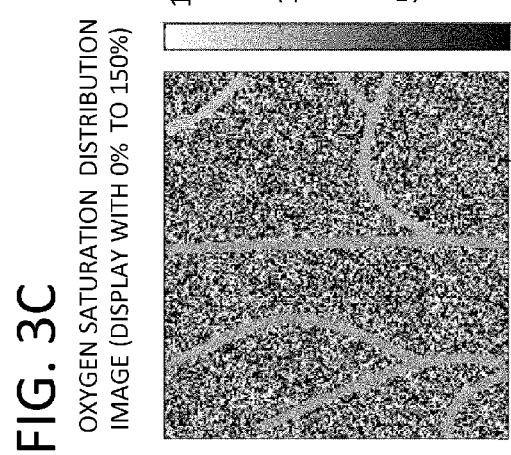

The processing flow of the present embodiment is the same as that in the first embodiment up to Step S103 in FIG. 2. In S104, color setting in which a displayed color flashes in each set value range is performed. In the present embodiment, it is described that only the abnormal value area flashes, but only the other value range may flash, and the individual value ranges may flash in turn. In addition, only one of the expected value and the suspended value may flash, and the expected value and the suspended value may flash alternately.

Figure 5:
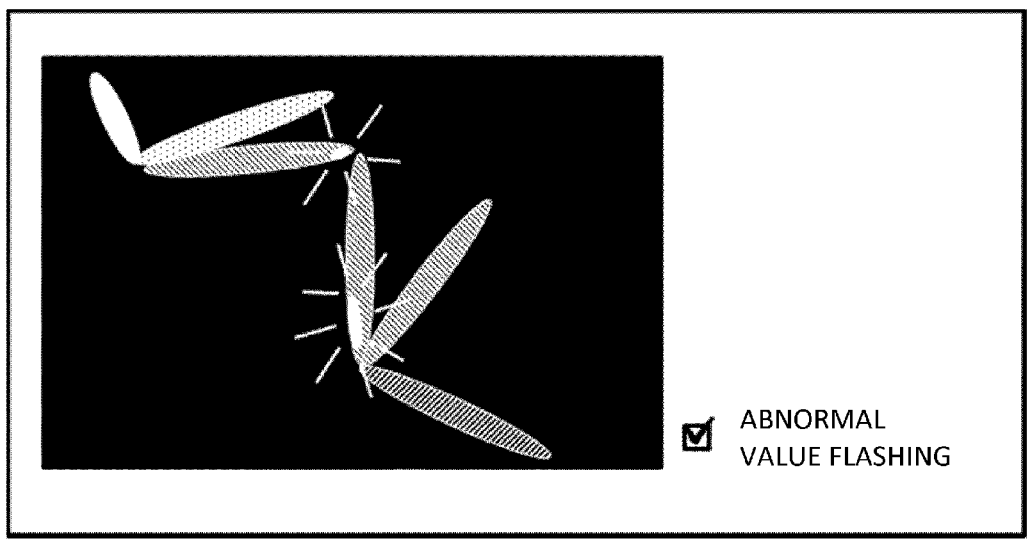
FIG. 5 is a schematic view showing an example of the display screen.

Further, a user interface shown in FIG. 5 may be displayed on a display screen. The user can select a flashing area by using the input unit 12. At this point, it is possible to select flashing/non-flashing and select a flashing display area by using a checkbox. In addition, part or all of the target area may be caused to flash by clicking the area with a cursor on the screen. In FIG. 5, the periphery of the flashing portion is emphasized using straight lines and viewability is thereby increased. While flashing is selected, each pixel of the target area on the screen flashes at a speed that allows determination of the operator. For example, the color display by the set color map and the color display according to "the other display method" are displayed for 0.5 seconds every second alternately.

In the present embodiment, as "the other display method", the color map in which the saturation (S) is set to 0% is used. However, the complementary color of the set color map may be automatically selected, or a color that is not used on the set color map may also be used. In addition, the color map in which the saturation (S) or the value (V) is set to 0% or 100% may be used as the other color. Further, as the other display method, any pattern may be displayed, or the saturation of the color on the set color map may be reduced as time elapses and the color is changed to the set other color as time elapses.

Subsequently, as the display method for distinguishing the individual value ranges, the case where part of one of the value ranges is displayed by using a texture image will be described. The texture image is a pattern for artificially expressing the texture and the pattern of the image by using visual changes. For example, in the case where the abnormal value area is expressed by using the texture image, by displaying the pattern having a different texture only in the abnormal value area portion, it is possible to distinguish the portion from the areas expressed with the uniform color map of the other areas.

Processing in and after S105 is the same as that in the first embodiment. Thus, in the present embodiment, in the area of the value range set in the display method setting unit 6, the special display method such as flashing is set. As a result, the determination of the area by the user is facilitated.

Third Embodiment

The object information acquisition apparatus of a third embodiment uses the same apparatus configuration as that in each of the first and second embodiments, and hence the detailed description of each configuration will be omitted. Hereinbelow, processing details in the signal processing unit 40 will be described with a focus on portions different from those in the above embodiments.

The object information acquisition apparatus of the present embodiment is capable of properly displaying the object image even in the case where a plurality of areas having different threshold values that serve as the boundary of the value ranges are present in the same object. Specifically, the apparatus theoretically calculates the threshold value for each area based on factors for the calculation error. Subsequently, the apparatus automatically sets each value range based on the calculated threshold value and displays it.

In the processing flow in FIG. 2, the same processing as that in the first embodiment is performed up to S102. Subsequently, in S103, the calculation error at each position of the oxygen saturation distribution is determined in the present embodiment. The calculation error of the oxygen saturation includes the error caused by the noise and the error caused by the background optical constant. The background optical constant is the average absorption coefficient and the equivalent scattering coefficient of the object, and these are pre-determined.

First, hereinbelow, the calculation error of the oxygen saturation caused by the noise will be described. Herein, as the noise, the error by a system noise is assumed. The flow of calculation of the calculation error of the oxygen saturation by the system noise is as follows. First, the system noise of the apparatus is measure and, subsequently, a noise signal intensity ratio (SN ratio) of the generated sound pressure in the case where a blood cell is assumed as the absorber is determined. Then, the calculation error of the absorption coefficient distribution or the oxygen saturation distribution is determined from the SN ratio of the initial sound pressure distribution.

First, the measurement is performed in the apparatus without placing the object, and the obtained signal is reconstructed and the initial sound pressure distribution is generated. Herein, one voxel is a cube 0.25 mm on a side, and the size of the initial sound pressure distribution is 200 voxels in length, 200 voxels in width, and 200 voxels in height. Note that, instead of performing the actual measurement, the noise can also be generated by a simulation in which the image reconstruction is performed with a system noise intensity observed by each probe used as an NEP (Noise Equivalent Pressure).

Next, the generated sound pressure of the blood cell at each position of the initial sound pressure distribution in the case where the blood cell is assumed as the absorber is determined. The blood cell having a radius of 1 mm is assumed as the absorber. By setting the Gruneisen constant of blood, the light amount distribution, and an absorption coefficient value of the radius of 1 mm, the generated sound pressure at each position of the initial sound pressure distribution is obtained from Expression (1). Herein, the Gruneisen constant of blood is set to 0.2, and the light amount distribution is calculated according to a light irradiation intensity distribution or an object shape. Specifically, the light amount distribution of the object was obtained by calculation by solving a light transport equation or a light diffusion equation. Note that, in the light transport equation or the light diffusion equation, methods that are already known in the field of numerical calculation such as the Monte Carlo method, difference calculus, and the finite element method can be used.

By using the initial sound pressure distributions of the obtained signal and noise, the absorption coefficient distributions are calculated from Expression (1). An SN distribution of the absorption coefficient distribution at each position of the object is obtained from the absorption coefficient distribution of the signal and the absorption coefficient distribution of the noise. By performing the calculation of the SN distribution of the absorption coefficient distribution at each position of the object with two wavelengths and performing calculation with the SN distributions, the SN distribution of the oxygen saturation is obtained. By calculating the variance of the oxygen saturation value at each position in the SN distribution of the oxygen saturation, the calculation error of the oxygen saturation distribution at each position of the object is determined.

Next, the calculation error of the oxygen saturation caused by the background optical constant will be described. Herein, consideration is given to the calculation of the calculation error of the oxygen saturation by the background optical constant by using a simulation. The estimation of the background optical constant is performed by using a measurement apparatus of the background optical constant. In the measurement apparatus, an estimated error of the background optical constant is assumed to be calculated, and the estimated error in this simulation is assumed to be ±5%. In this case, in each measurement of the background optical constant, it is possible to consider that the estimated error is superimposed on the measurement result.

As the object, when one voxel is a cube 0.25 mm on a side, volume data that is 200 voxels in length, 200 voxels in width, and 200 voxels in height is considered. It is assumed that, in the entire volume data, the average scattering coefficient and the average absorption coefficient (background optical constant) of an interstitial tissue of a biological body are set. In the case where the object is measured using the measurement apparatus and the acquired background optical constant is equal to the average scattering coefficient and the average absorption coefficient, the measurement error of the background optical constant is ±5%. Accordingly, the value range of the background optical constant including the error can be calculated.

Next, the light amount distribution of the object is determined by using the background optical constant including the error. It is also possible to obtain the light amount distribution by solving the light transport equation or the light diffusion equation. From these, it is possible to acquire the absorption coefficient distribution of the object.

The oxygen saturation distribution is calculated by performing the above process with two wavelengths. By calculating deviation from the true value of the background optical constant, it is possible to calculate the calculation error of the oxygen saturation distribution in the object area. By totalizing the calculation errors of the oxygen saturation by the noise and the background optical constant obtained in this manner, it is possible to calculate the calculation error of the oxygen saturation at each position of the object. In the case of totalizing the calculation errors, it is desirable to perform root mean square of errors of a plurality of factors at each position of the object, but addition of the error may also be appropriately performed.

Subsequently, in the display method setting unit 6, the threshold value at each position of the object is set. Herein, in the case where a two-dimensional image (a cross section image in one axis of the length, width, and height of the object or an image having a thickness of a plurality of voxels) is displayed in the display unit 7, there is a possibility that the threshold value (or the value range) differs from one position of the object to another. In this case, for example, the maximum threshold value in each cross section image is used.

Processing in and after S104 is the same as that in the first embodiment.

Thus, in the present embodiment, the threshold value that separates the individual value ranges of the concentration relating distribution is set according to the calculation error of the concentration relating distribution at each position of the calculated concentration relating distribution. As a result, it is possible to separate the individual value ranges with excellent accuracy.

Fourth Embodiment

Next, a fourth embodiment will be described with a focus on portions different from those in the above embodiments. The object information acquisition apparatus of the present embodiment calculates a calculation error map of a blood glucose concentration distribution at each position in the case where the concentration relating distribution is the blood glucose concentration distribution.

Figure 6:
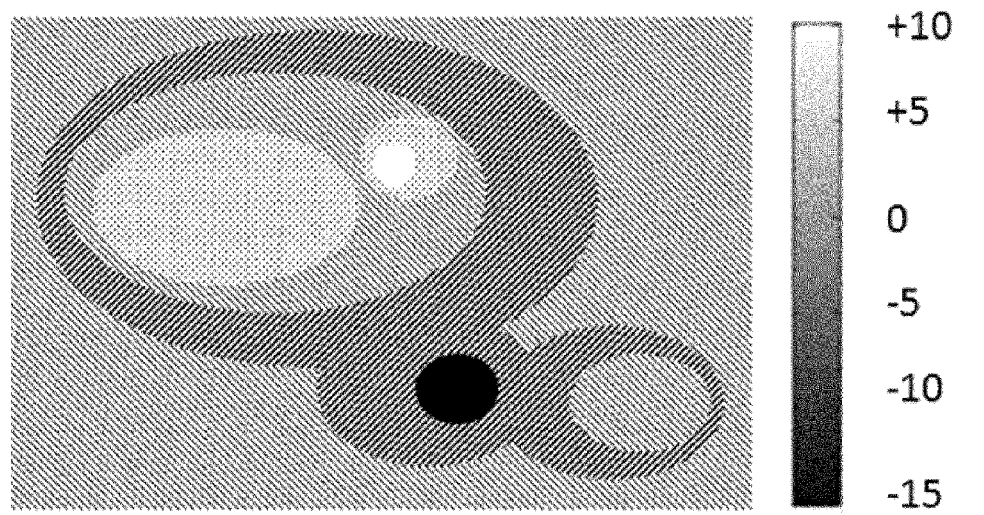
FIG. 6 is a schematic view showing an example of the display screen.

In S103 in the processing flow in FIG. 2, processing until the error at each position of the blood glucose concentration distribution is calculated is the same as that in the third embodiment. With this, it is possible to calculate a calculation error distribution indicative of the error at each position of the blood glucose concentration distribution. By displaying the calculation error distribution in the display unit 7 in S104, it is possible to display the calculation error distribution at each position of the blood glucose concentration distribution at each position of the object. At this point, as shown in FIG. 6, the percentage of the calculation error of the blood glucose concentration distribution in a given cross section may be expressed by using a contour figure. In addition, other drawing methods may also be used.

Thus, in the present embodiment, it is possible to realize reliability at each position of the calculated concentration relating distribution by visualizing the calculation error of the concentration relating distribution at each position of the calculated concentration relating distribution.

Fifth Embodiment

Next, a fifth embodiment will be described with a focus on portions different from those in the above embodiments. The object information acquisition apparatus of the present embodiment selectively displays at least one of the expected value area, the suspended value area, and the abnormal value area of the concentration relating information distribution. Herein, as the concentration relating distribution, a molecular probe concentration distribution is used.

In S102 in the processing flow in FIG. 2, the concentration relating information distribution is calculated. In the display method setting unit 6, the value ranges of the expected value and the suspended value are determined according to empirically obtained value ranges (e.g., 0 to 100%, 100 to 110%). The value range other than the above value ranges is determined as the value range of the abnormal value. Further, in S104, at least one of the expected value area, the suspended value area, and the abnormal value area of the concentration relating information distribution is displayed. The area to be displayed may be a predetermined area, and the area may be switched according to the instruction that uses the input unit 12. Note that, for the value range other than the display target, a display method that allows easy recognition of the value range such as a display method in which the value range is displayed in the same color as the background color is preferable.

In the present embodiment, it is possible to easily determine the distribution of each value range of the concentration relating information distribution. In particular, by using the value set according to the empirical rule or the like, it becomes possible to display the concentration relating information distribution without calculation processing by the apparatus.

According to the present invention, even in the case where the calculation errors caused by the noise, the reconstruction artifact, and the background optical constant are included in the distribution relating to calculated optical characteristics of the object, it becomes possible to determine the abnormal value of the concentration relating distribution such as the oxygen saturation distribution. As a result, the diagnostic performance of the displayed concentration relating distribution is improved.

Other Embodiments

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application is a National Phase of PCT Application No. PCT/JP2016/068585 filed Jun. 16, 2016, which in turn claims the benefit of Japanese Patent Application No. 2015-125787, filed Jun. 23, 2015, which are hereby incorporated by reference herein in their entirety.

The invention claimed is:

1. An information processing apparatus comprising:
a first acquisition unit configured to acquire information relating to an oxygen saturation distribution in an object;
a determination unit configured to determine, based on the information relating to the oxygen saturation distribution, whether calculated values of oxygen saturation at each of a plurality of positions are included in a first numerical range from 100% to a first value more than 100%, or a second numerical range in which an included value is more than the first value; and
a display control unit and a display unit, said display control unit being configured to cause said display unit to display an image of the oxygen saturation distribution so as to distinguish whether the calculated values of oxygen saturation at each of the plurality of positions are included in the first or the second numerical range based on a determination result of the determination unit, wherein
the display control unit is configured to cause the display unit to display the image of the oxygen saturation distribution so that calculated values of the oxygen saturation in the first numerical range are displayed as 100%.

2. The apparatus according to claim 1, wherein the display control unit is configured to prevent the display unit from displaying an image of the position at which the calculated value of oxygen saturation is in the second numerical range.

3. The apparatus according to claim 1, wherein the display control unit is configured to cause the display unit to display the first and second numerical ranges with different color scales.

4. The apparatus according to claim 3, wherein the display control unit is configured to assign, to the first numerical range, a color scale in which a color is continuously changed from a color assigned in a case where the oxygen saturation is 100%.

5. The apparatus according to claim 4, wherein the display control unit is configured to assign, in the first numerical range, the color scale such that a chroma is continuously reduced while the oxygen saturation reaches the first value from 100%.

6. The apparatus according to claim 5, wherein the display control unit is configured to set the chroma to 0 when the oxygen saturation has the first value and when the oxygen saturation is in the second numerical range.

7. The apparatus according to claim 4, wherein the display control unit is configured to fix a hue in the first numerical range.

8. The apparatus according to claim 3, wherein the display control unit is configured to assign a single color to the second numerical range.

9. The apparatus according to claim 1, wherein the display control unit is configured to cause one of the first numerical range and the second numerical range to flash.

10. The apparatus according to claim 1, wherein the display control unit is configured to cause the display unit to display an annotation that provides notification of at least one of an area of the first numerical range and an area of the second numerical range.

11. The apparatus according to claim 1, further comprising a second acquisition unit configured to acquire information relating to the first value determined based on an instruction of a user.

12. The apparatus according to claim 1, wherein the display control unit is configured to perform control capable of distinguishing a third numerical range in which the oxygen saturation is 0 to 100%, the first numerical range, and the second numerical range.

13. The apparatus according to claim 1, wherein the display control unit is configured to extract a spatial distribution of a blood vessel portion and cause the display unit to display the spatial distribution of the blood vessel portion.

14. The apparatus according to claim 1, further comprising:
   a light irradiation unit configured to apply light to an object; and
   a reception unit configured to receive an acoustic wave generated from the object to which the light is applied to thereby output a signal, wherein
   the first acquisition unit is configured to acquire the information relating to the oxygen saturation distribution by using the signal.

15. The apparatus according to claim 1, wherein the display control unit is configured to prevent the display unit from displaying the calculated value of the oxygen saturation in the second numerical range.

16. A display control method for an image of an oxygen saturation distribution, comprising the steps of:
   causing a display unit to display the image of the oxygen saturation distribution so as to distinguish between a position corresponding to a numerical range in which a calculated value of an oxygen saturation is from 100% to a first value more than 100% and a position corresponding to a second numerical range in which the calculated value of the oxygen saturation is more than the first value; and
   causing the display unit to display the image of the oxygen saturation distribution so that calculated values of the oxygen saturation in the first numerical range are displayed as 100%.

17. The display control method according to claim 16, wherein, in the step of causing the display unit to display the image, the position at which the calculated value of the oxygen saturation is included in a first numerical range from 100% to the first value as the position at which the oxygen saturation is 100% is displayed.

18. The display control method according to claim 17, wherein, in the step of causing the display unit to display the image, the position at which the calculated value of the oxygen saturation is included in the second numerical range is not displayed.

19. A non-transitory computer readable storage medium that stores a program for causing an information processing apparatus to execute a display control method comprising the steps of:
   causing a display unit to display the image of the oxygen saturation distribution so as to distinguish between a position corresponding to a numerical range in which a calculated value of an oxygen saturation is from 100% to a first value more than 100% and a position corresponding to a second numerical range in which the calculated value of the oxygen saturation is more than the first value; and
   causing the display unit to display the image of the oxygen saturation distribution so that calculated values of the oxygen saturation in the first numerical range are displayed as 100%.

* * * * *